United States Patent
Palmer

(10) Patent No.: US 10,258,803 B2
(45) Date of Patent: Apr. 16, 2019

(54) RADIO FREQUENCY TRANSMITTER CIRCUITS THAT PROVIDE POWER TO AN IMPLANT DEVICE

(71) Applicant: ADVANCED BIONICS AG, Staefa (CH)

(72) Inventor: Logan P. Palmer, Santa Monica, CA (US)

(73) Assignee: Advanced Bionics AG, Staefa (CH)

( * ) Notice: Subject to any disclaimer, the term of this patent is extended or adjusted under 35 U.S.C. 154(b) by 164 days.

(21) Appl. No.: 15/315,357

(22) PCT Filed: Jun. 30, 2014

(86) PCT No.: PCT/US2014/044974
§ 371 (c)(1),
(2) Date: Nov. 30, 2016

(87) PCT Pub. No.: WO2016/003437
PCT Pub. Date: Jan. 7, 2016

(65) Prior Publication Data
US 2017/0189694 A1    Jul. 6, 2017

(51) Int. Cl.
| | |
|---|---|
| *A61N 1/378* | (2006.01) |
| *H02J 7/00* | (2006.01) |
| *H03F 3/217* | (2006.01) |
| *H02J 50/12* | (2016.01) |
| *A61N 1/36* | (2006.01) |
| *A61N 1/372* | (2006.01) |
| *A61N 1/02* | (2006.01) |
| *A61N 1/05* | (2006.01) |

(52) U.S. Cl.
CPC ........... *A61N 1/3787* (2013.01); *A61N 1/025* (2013.01); *A61N 1/0541* (2013.01); *A61N 1/36036* (2017.08); *A61N 1/37276* (2013.01); *H02J 7/0054* (2013.01); *H02J 50/12* (2016.02); *H03F 3/217* (2013.01)

(58) Field of Classification Search
CPC .............. A61N 1/3787; A61N 1/36036; A61N 1/37276; A61N 1/0541; A61N 1/025; H02J 7/0054; H02J 50/12; H03F 3/217
See application file for complete search history.

(56) References Cited

U.S. PATENT DOCUMENTS

| | | |
|---|---|---|
| 6,294,957 B1 | 9/2001 | Luu |
| 7,016,738 B1 | 3/2006 | Karunasiri |

(Continued)

FOREIGN PATENT DOCUMENTS

CN    202918267 U    5/2013

OTHER PUBLICATIONS

Dudek, et al., "A High-Resolution CMOS Time-to-Digital Converter Utilizing a Vernier Delay Line", *IEEE Transactions on Solid-State Circuits*, vol. 35, No. 2, Feb. 2000, 240-247.

(Continued)

*Primary Examiner* — Mark Bockelman
(74) *Attorney, Agent, or Firm* — ALG Intellectual Property, LLC

(57) ABSTRACT

Exemplary radio frequency (RF) transmitter circuits that provide power to an implant device are described. An exemplary RF transmitter circuit may be included in an apparatus located external to a patient and may be configured to dynamically adjust an amount of power that is provided to an implant device implanted within the patient.

20 Claims, 9 Drawing Sheets

(56) References Cited

U.S. PATENT DOCUMENTS 7,715,493 B2  5/2010  Ravi
8,275,462 B1  9/2012  Griffith

OTHER PUBLICATIONS

International Search Report and Written Opinion received in International Application No. PCT/US14/044974, dated Sep. 23, 2014.

RADIO FREQUENCY TRANSMITTER CIRCUITS THAT PROVIDE POWER TO AN IMPLANT DEVICE

BACKGROUND INFORMATION

Cochlear implants and other implantable medical devices are commonly powered from a battery included in an external device (e.g., a speech processor apparatus) through a radio frequency ("RF") inductive link. To minimize the size of the external device and to maximize battery life, an RF power transmitter included in the external device needs to be physically small, electrically efficient, and adjustable in small increments in order to optimize the power delivery for the stimulation requirements at any given moment. In particular, cochlear implants require frequent and fine resolution power adjustments to maximize power efficiency within the users' dynamically changing audio environments.

In some conventional cochlear implant systems, the RF power transmitter consists of two parts. A class-D power amplifier is implemented in a CMOS integrated circuit, and this provides small size and good efficiency. However, in order to provide fine resolution power adjustments (e.g., 256 steps), an adjustable inductive switching regulator is used, which requires a separate integrated circuit and a large off-chip inductor. This has a negative impact on the overall size of the RF power transmitter, and hence, the external device.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
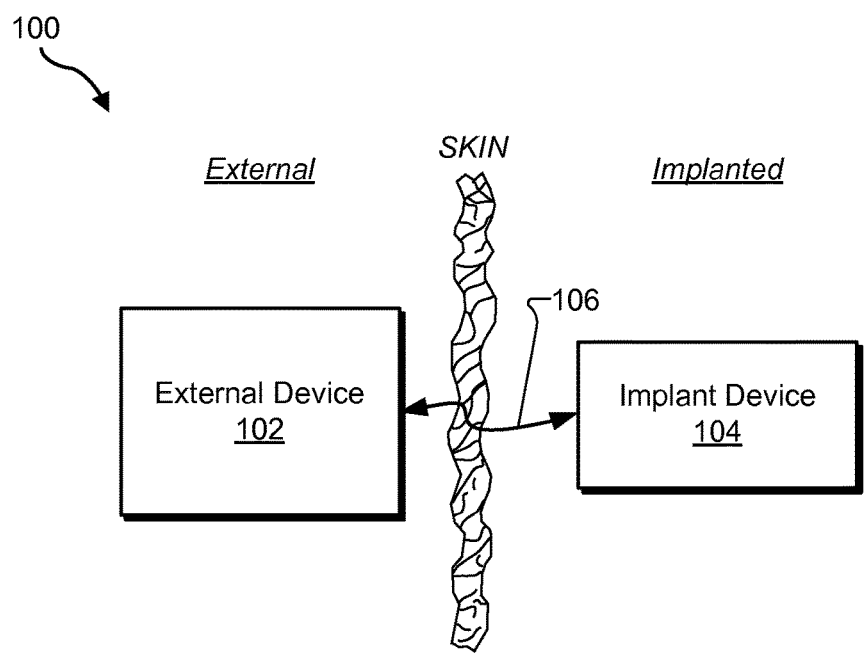
FIG. 1 shows an exemplary implantable medical device system according to principles described herein.

Exemplary RF transmitter circuits that provide power to an implant device are described herein. An exemplary RF transmitter circuit as described herein may be included in an apparatus (e.g., a sound processor apparatus that is a part of an auditory prosthesis system) located external to a patient and may be configured to dynamically adjust an amount of power that is provided to an implant device (e.g., a cochlear implant) implanted within the patient.

To illustrate, an exemplary RF transmitter circuit may include first and second delay-locked loop circuits, first and second switching circuits, and a transformer circuit. The first delay-locked loop circuit may receive a clock signal, generate a first set of phase shifted clock signals each phase shifted relative to the clock signal by a different phase delay increment included in a first set of phase delay increments, and output, in accordance with a first delay control signal, a first phase shifted clock signal included in the first set of phase shifted clock signals and that is phase shifted relative to the clock signal by a first phase delay increment included in the first set of phase delay increments. Likewise, the second delay-locked loop circuit may receive the clock signal, generate a second set of phase shifted clock signals each phase shifted relative to the clock signal by a different phase delay increment included in a second set of phase delay increments, and output, in accordance with a second delay control signal, a second phase shifted clock signal included in the second set of phase shifted clock signals and that is phase shifted relative to the clock signal by a second phase delay increment included in the second set of phase delay increments. The first switching circuit may receive the first phase shifted clock signal from the first delay-locked loop circuit and output a first switch signal based on the first phase shifted clock signal, the first switch signal being phase shifted relative to the clock signal by the first phase delay increment. Likewise, the second switching circuit may receive the second phase shifted clock signal from the second delay-locked loop circuit and output a second switch signal based on the second phase shifted clock signal, the second switch signal being phase shifted relative to the clock signal by the second phase delay increment. The transformer circuit may use the first and second switch signals to generate an RF signal for transmission to an implant device implanted in the patient. As will be described below, the RF signal may provide power for the implant device and may have a power level that is set based on the first and second phase delay increments.

As will be described in more detail below, the RF transmitter circuits described herein may employ a vernier delay scheme, which may facilitate relatively fine resolution power level adjustment of the RF signals output by the RF transmitter circuits. Moreover, each RF transmitter circuit described herein may be implemented in a CMOS integrated circuit, which may advantageously provide small size and relatively good efficiency. Another benefit of the RF transmitter circuits described herein is that they are predictable and consistent across all manufactured instances of the RF transmitter circuits. This may minimize the calibration and/or trimming needed during production testing and/or field use.

FIG. 1 shows an exemplary implantable medical device system 100 ("system 100") within which the RF transmitter circuits described herein may be employed. As shown, system 100 may include an external device 102 located external to a patient and an implant device 104 implanted within the patient.

Implant device 104 may be implemented by any suitable implantable medical device that receives power from and/or is controlled by external device 102. For example, implant device 104 may be implemented by a cochlear implant and/or any other type of implantable stimulator.

External device 102 may be implemented by any device or apparatus configured to provide power to and/or control implant device 104. For example, external device 102 may be implemented by a speech processor apparatus, a battery module, and/or any other suitable device as may serve a particular implementation.

In some examples, external device 102 may provide power (e.g., operating power) to implant device 104 by way of a wireless link 106. The power may be provided in any suitable manner. For example, the power may be provided in the form of an RF signal that is wirelessly transmitted (e.g., transcutaneously) to implant device 104. As will be described below, external device 102 may vary the amount of power provided to implant device 104 by varying the power level of the RF signal that is transmitted by way of wireless link 106. Wireless link 104 may include a bi-directional communication link and/or one or more dedicated uni-directional communication links as may serve a particular implementation.

In some examples, external device 102 may also transmit data (e.g., control parameters) to implant device 104 by way of wireless link 106. For example, external device 102 may modulate data onto the RF signal used to provide power to implant device 104. In this manner, data and power may be transmitted using the same RF signal.

Figure 2:
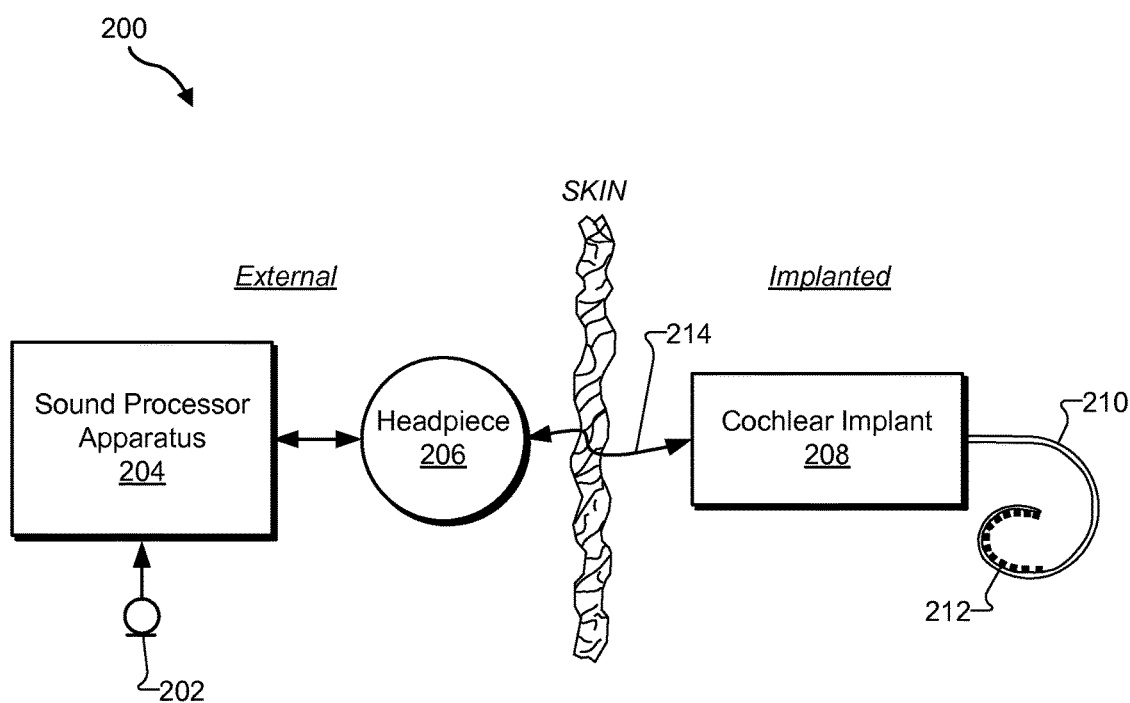
FIG. 2 illustrates an exemplary auditory prosthesis system according to principles described herein.

FIG. 2 illustrates an exemplary implementation of system 100, and shows an exemplary auditory prosthesis system 200. As shown, auditory prosthesis system 200 may include various components configured to be located external to a patient including, but not limited to, a microphone 202, a sound processor apparatus 204, and a headpiece 206. Auditory prosthesis system 200 may further include various components configured to be implanted within the patient including, but not limited to, a cochlear implant 208 and a lead 210 with a plurality of electrodes 212 disposed thereon. As will be described in more detail below, additional or alternative components may be included within auditory prosthesis system 200 as may serve a particular implementation. In some examples, external device 102 may be implemented by sound processor apparatus 204 and implant device 104 may be implemented by cochlear implant 208. The components shown in FIG. 2 will now be described in more detail.

Microphone 202 may be configured to detect audio signals presented to the patient. Microphone 202 may be implemented in any suitable manner. For example, microphone 202 may include and/or represent a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor apparatus 204. Additionally or alternatively, microphone 202 may be implemented by one or more microphones disposed within headpiece 206, one or more microphones disposed within sound processor apparatus 204, and/or any other suitable microphone as may serve a particular implementation.

Sound processor apparatus 204 (i.e., one or more components included within sound processor apparatus 204) may be configured to direct cochlear implant 208 to generate and apply electrical stimulation (also referred to herein as "stimulation current") representative of one or more audio signals (e.g., one or more audio signals detected by microphone 202, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor apparatus 204 may process the one or more audio signals in accordance with a selected sound processing strategy or program to generate appropriate stimulation parameters for controlling cochlear implant 208. Sound processor apparatus 204 may include or be implemented by a behind-the-ear ("BTE") unit, a body worn device, and/or any other sound processing unit as may serve a particular implementation.

In some examples, sound processor apparatus 204 may wirelessly transmit stimulation parameters (e.g., in the form of data words included in a forward telemetry sequence) and/or power signals to cochlear implant 208 by way of a wireless communication link 214 between headpiece 206 and cochlear implant 208. It will be understood that wireless communication link 214 may include a bi-directional communication link and/or one or more dedicated uni-directional communication links.

Headpiece 206 may be communicatively coupled to sound processor apparatus 204 and may include an external antenna (e.g., a coil and/or one or more wireless communication components) configured to facilitate selective wireless coupling of sound processor apparatus 204 to cochlear implant 208. Headpiece 206 may additionally or alternatively be used to selectively and wirelessly couple any other external device to cochlear implant 208. To this end, headpiece 206 may be configured to be affixed to the patient's head and positioned such that the external antenna housed within headpiece 206 is communicatively coupled to a corresponding implantable antenna (which may also be implemented by a coil and/or one or more wireless communication components) included within or otherwise associated with cochlear implant 208. In this manner, stimulation parameters and/or power signals may be wirelessly transmitted between sound processor apparatus 204 and cochlear implant 208 via a wireless communication link 214 (which may include a bi-directional communication link and/or one or more dedicated uni-directional communication links as may serve a particular implementation).

Cochlear implant 208 may include any type of implantable stimulator that may be used in association with the systems and methods described herein. For example, cochlear implant 208 may be implemented by an implantable cochlear stimulator. In some alternative implementations, cochlear implant 208 may include a brainstem implant and/or any other type of cochlear implant that may be implanted within a patient and configured to apply stimulation to one or more stimulation sites located along an auditory pathway of a patient.

In some examples, cochlear implant 208 may be configured to generate electrical stimulation representative of an audio signal processed by sound processor apparatus 204 (e.g., an audio signal detected by microphone 202) in accordance with one or more stimulation parameters transmitted thereto by sound processor apparatus 204. Cochlear implant 208 may be further configured to apply the electrical stimulation to one or more stimulation sites within the patient via one or more electrodes 212 disposed along lead 210. In some examples, cochlear implant 208 may include a plurality of independent current sources each associated with a channel defined by one or more of electrodes 212. In this manner, different stimulation current levels may be applied to multiple stimulation sites simultaneously by way of multiple electrodes 212.

The auditory prosthesis system 200 illustrated in FIG. 2 may be referred to as a cochlear implant system because sound processor apparatus 204 is configured to direct cochlear implant 208 to generate and apply electrical stimulation representative of audio content (e.g., one or more audio signals) to one or more stimulation sites within the patient by way of one or more of electrodes 212. Auditory prosthesis system 200 may alternatively be implemented by an electro-acoustic stimulation ("EAS") system configured to provide both electrical stimulation by way of cochlear implant 208 and acoustic stimulation by way of a receiver or loudspeaker (not shown) connected to sound processor apparatus 204.

Figure 3:
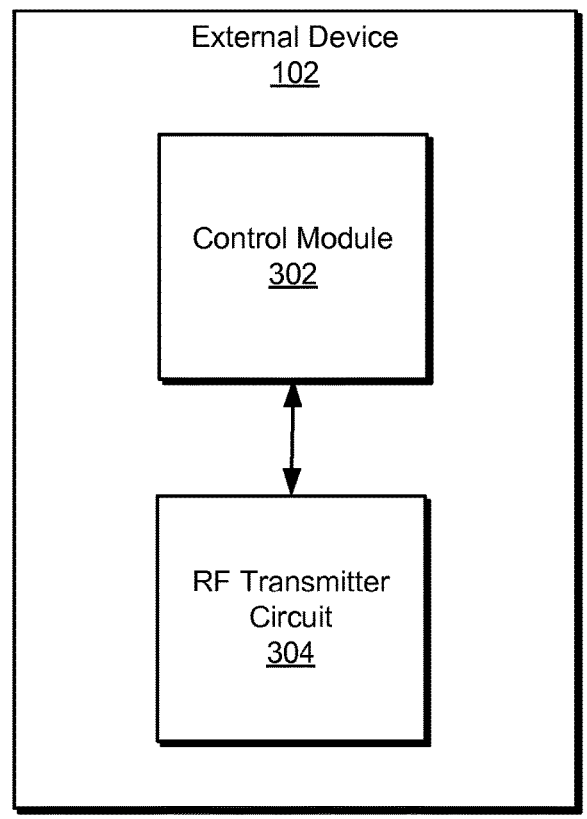
FIG. 3 shows exemplary components that may be included within an external device according to principles described herein.

FIG. 3 shows exemplary components that may be included within external device 102 (e.g., within sound processor apparatus 204). As shown, external device 102 may include a control module 302 and an RF transmitter circuit 304 communicatively coupled one to another. It will be recognized that external device 102 may include additional or alternative components as may serve a particular implementation. In some examples, one or more of the components included in sound processor apparatus 104 (e.g., control module 302 and RF transmitter circuit 304) may be housed within a single casing.

Control module 302 may be implemented by any suitable combination of integrated circuits, circuitry, processors, and/or computing devices configured to perform one or more of the operations and/or functions described herein.

Control module 302 may be configured to perform one or more operations with respect to one or more components connected to or otherwise communicatively coupled to external device 102. For example, control module 302 may be configured to control an operation of implant device 104. To illustrate, in cases where external device 102 is implemented by sound processor apparatus 204, control module 302 may process an audio signal presented to a patient, generate one or more stimulation parameters based on the processing of the audio signal, and direct cochlear implant 208 to generate and apply electrical stimulation representative of the audio signal to the patient in accordance with the stimulation parameters (e.g., by transmitting the stimulation parameters to cochlear implant 208).

Control module 302 may also be configured to control an operation of RF transmitter circuit 304. For example, as will be described in more detail below, control module 302 may direct RF transmitter circuit 304 to dynamically adjust a power level of an RF signal output by RF transmitter circuit 304.

RF transmitter circuit 304 may be configured to generate and output an RF signal (also referred to as a high frequency carrier signal, or simply a carrier signal) that provides power to implant device 104. For example, RF transmitter circuit 304 may generate an RF signal by generating a first switch signal that is phase shifted relative to a clock signal by a first phase delay increment, generating a second switch signal that is phase shifted relative to the clock signal by a second phase delay increment that is different than the first phase delay increment, and applying the first and second switch signals to a transformer operating in a push-pull configuration. In some examples, control module 302 may direct RF transmitter circuit 304 to dynamically adjust a power level of the RF signal by directing RF transmitter circuit 304 to adjust at least one of the first phase delay increment and the second phase delay increment. This will be described in more detail below.

Figure 4:
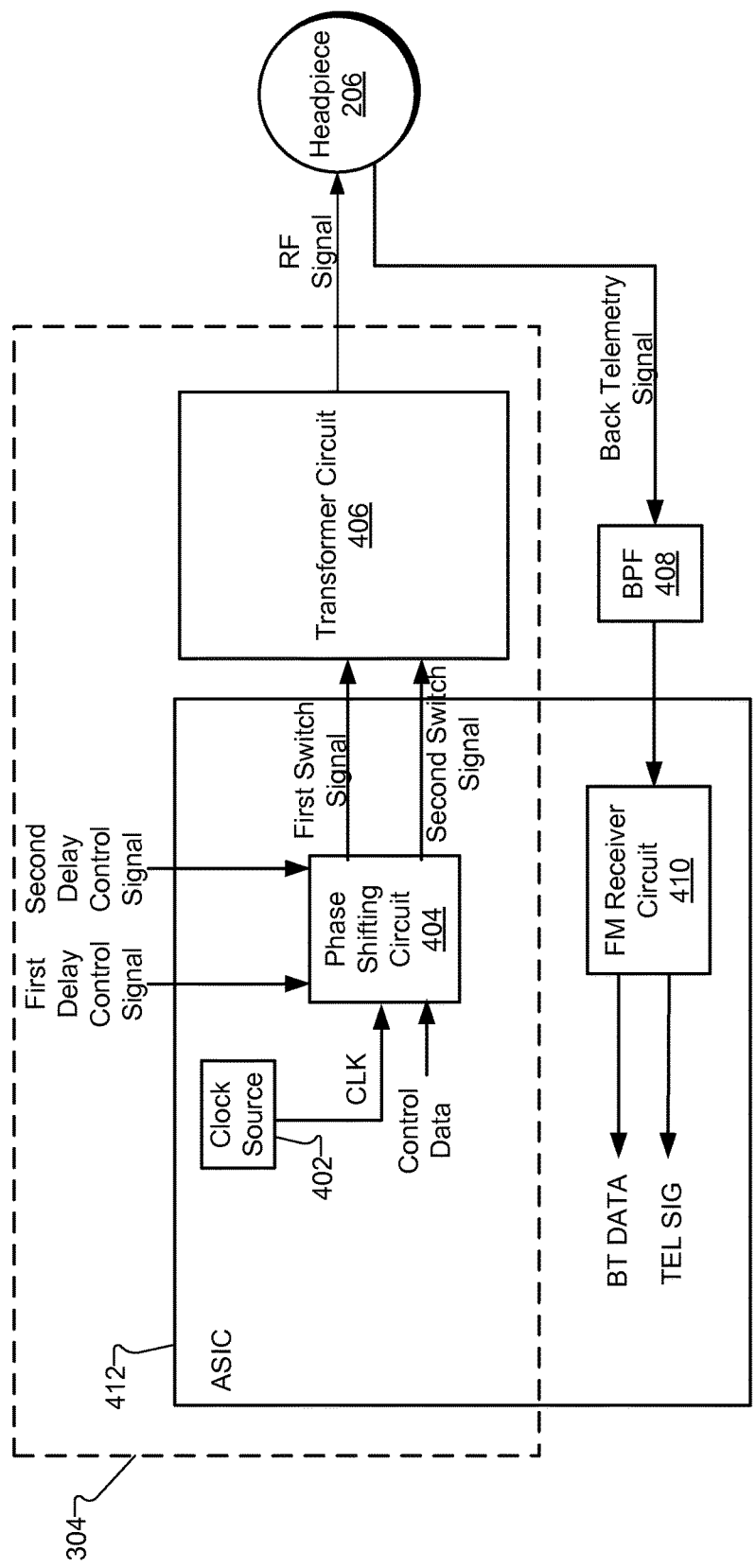
FIG. 4 shows a block diagram of an RF transmitter circuit and other components that may be housed within an external device according to principles described herein.

FIG. 4 shows a block diagram of RF transmitter circuit 304 and other components that may be housed within external device 102. In this example, RF transmitter circuit 304 is configured to be included in a speech processor apparatus that is a part of an auditory prosthesis system. As shown in FIG. 4, RF transmitter circuit 304 may include a clock source 402, a phase shifting circuit 404, and a transformer circuit 406. Each of these components will now be described.

Clock source 402 may generate and provide a clock signal ("CLK"). Clock source 402 may include any suitable clock source, such as an oscillator circuit. The clock signal output by clock source 402 may be a digital signal that has any suitable frequency. For example, the clock signal may have a frequency of 49 MHz. In some examples, the clock signal may vary within a predetermined range of frequencies. Such range of frequencies may be suitable, for example, for narrow band modulation, frequency modulation, amplitude modulation, and/or any other suitable type of modulation.

As shown, the clock signal output by clock source 402 may be received by phase shifting circuit 404, which may use the clock signal to generate and output first and second switch signals. As will be described below, the first and second switch signals may both be phase shifted by different amounts with respect to the clock signal. The amount of phase shifting for each of the first and second switch signals may be set in accordance with first and second delay control signals provided by control module 302, which control signals are shown in FIG. 4 as being received by phase shifting circuit 404. Exemplary manners in which the phase shifting is set for the first and second switch signals will be described in more detail below.

As shown, the first and second switch signals are received by transformer circuit 406, which is configured to use the first and second switch signals to generate and output an RF signal for transmission to implant device 104. The application of these signals to transformer circuit 406 may result in a push-pull mode of operation. For example, transformer circuit 406 generates an RF signal having an amplitude that varies as a function of the phase shift between the first and second switch signals. The power level of the RF signal may be set (e.g., adjusted), as desired, to assume various values by controlling the first and second delay control signals.

If desired, an amplifier (not shown) may be used to further control the power level of the RF signal. Such an amplifier may receive the RF signal from transformer circuit 406 and provide an amplified variant of that signal to headpiece 206. The amplification of the RF signal may be fixed or variable. In fixed amplification embodiments, control of the RF signal amplitude may be controlled by phase shifting circuit 404. In variable amplification embodiments, control of the RF signal amplitude may be controlled by phase shifting circuit 404 and/or the amplifier.

In some examples, control data may be provided to phase shifting circuit 404 and modulated onto the RF signal output by transformer circuit 406. For example, an amplitude-shift-keyed ("ASK") modulation scheme may be used to modulate data onto the RF signal.

As shown, transformer circuit 406 may provide the RF signal to a coil within headpiece 206, where it is transmitted as a forward carrier signal to implant device 104. Transformer circuit 406 is described more fully in U.S. Pat. No. 8,275,462, which is incorporated herein by reference in its entirety.

In some examples, headpiece 206 may also include an antenna coil tuned to receive a back telemetry signal from implant device 104. In some embodiments, in order to simplify the design of external device 102, the back telemetry feature may be omitted. When used, such a back telemetry signal may be modulated with data provided by implant device 104, and may be at a different carrier frequency than is the forward carrier signal transmitted to implant device 104. For example, in one embodiment, where the forward carrier signal operates at a fixed frequency of 49 MHz, the back telemetry signal may have a fixed carrier frequency of 10.7 MHz. An example of one type of modulation used to modulate the back telemetry signal may be frequency modulation (FM), but other types of modulation can also be used.

The back telemetry signal may be routed through a separate transformer circuit (not shown) and applied to a first bandpass filter circuit ("BPF") 408. The filtered back telemetry signal is then directed to an FM receiver circuit 410. FM receiver circuit 410 detects and demodulates the back telemetry signal. As a result of such demodulation, FM receiver circuit 410 may generate a data signal ("BT DATA") that represents the demodulated data received through the back telemetry signal and a signal ("TEL SIG") that identifies the presence of a back telemetry signal within FM receiver circuit 410. The presence of the TEL SIG signal may thus be used to identify that a link has been established with implant device 104. Knowing that a link has been established with implant device 104 may, in turn, be used for various purposes (such as a power control feedback loop).

In some examples, clock source 402, phase shifting circuit 404, and FM receiver circuit 410 may all be formed or embedded within the same application specific integrated circuit ("ASIC") 412. ASIC 412 may also include one or more other digital circuits associated with external device 102, such as one or more circuits that implement control module 302. ASIC 412 may be mounted on a suitable printed circuit board ("PCB") within external device 102. Other discrete components, not part of ASIC 412, may also be mounted on the PCB or otherwise housed within external device 102.

Figure 5:
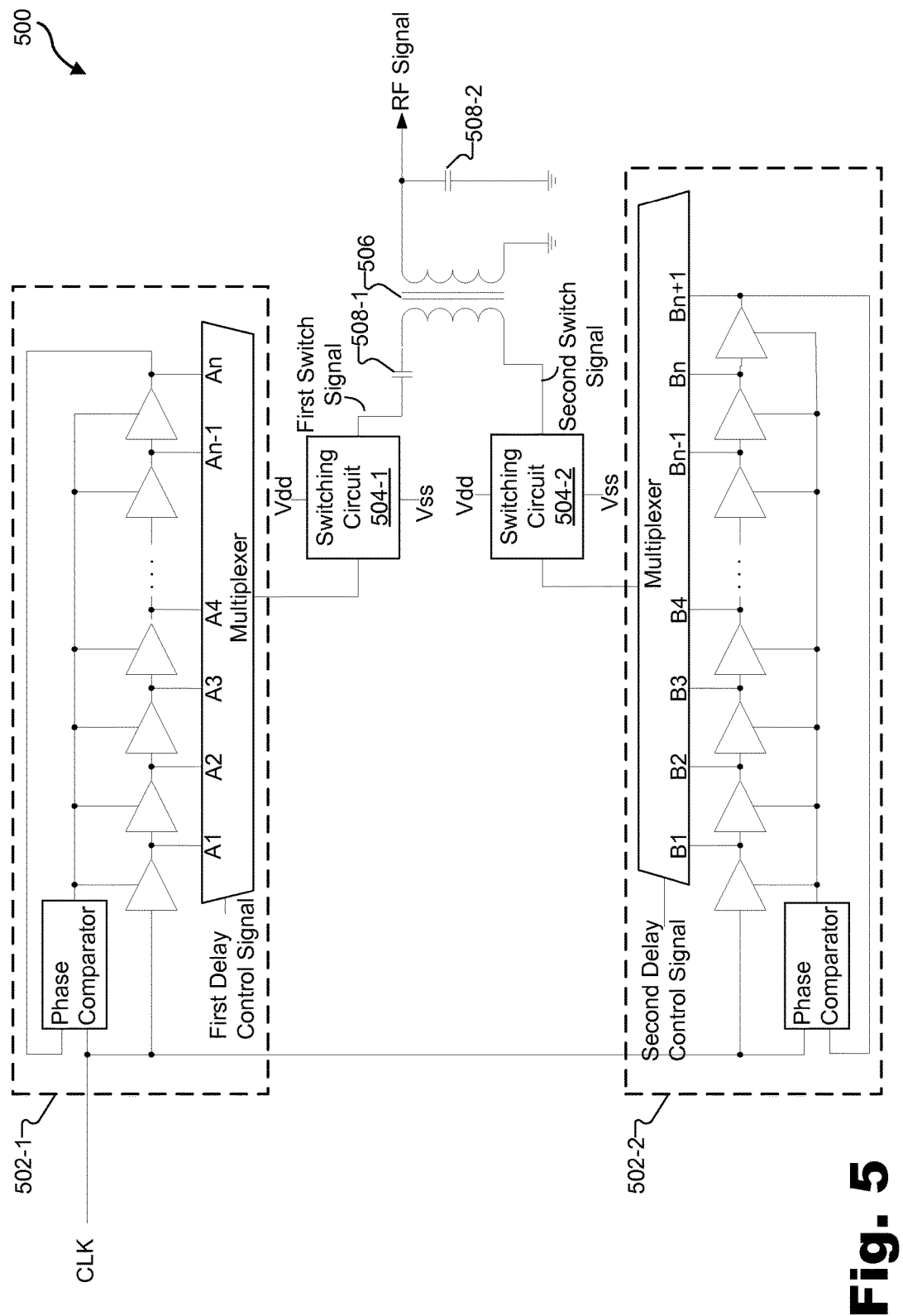
FIG. 5 show an exemplary implementation of a phase shifting circuit and a transformer circuit according to principles described herein.

FIG. 5 show an exemplary implementation 500 of phase shifting circuit 404 and transformer circuit 406. As shown, implementation 500 may include first and second delay-locked loop ("DLL") circuits 502-1 and 502-2 (collectively "DLL circuits 502"), first and second switching circuits 504-1 and 504-2 (collectively "switching circuits 504"), a transformer 506, and capacitors 508-1 and 508-2 (collectively "capacitors 508"). DLL circuits 502 and switching circuits 504 implement phase shifting circuit 404. Transformer 506 and capacitors 508 implement transformer circuit 406.

Figure 6:
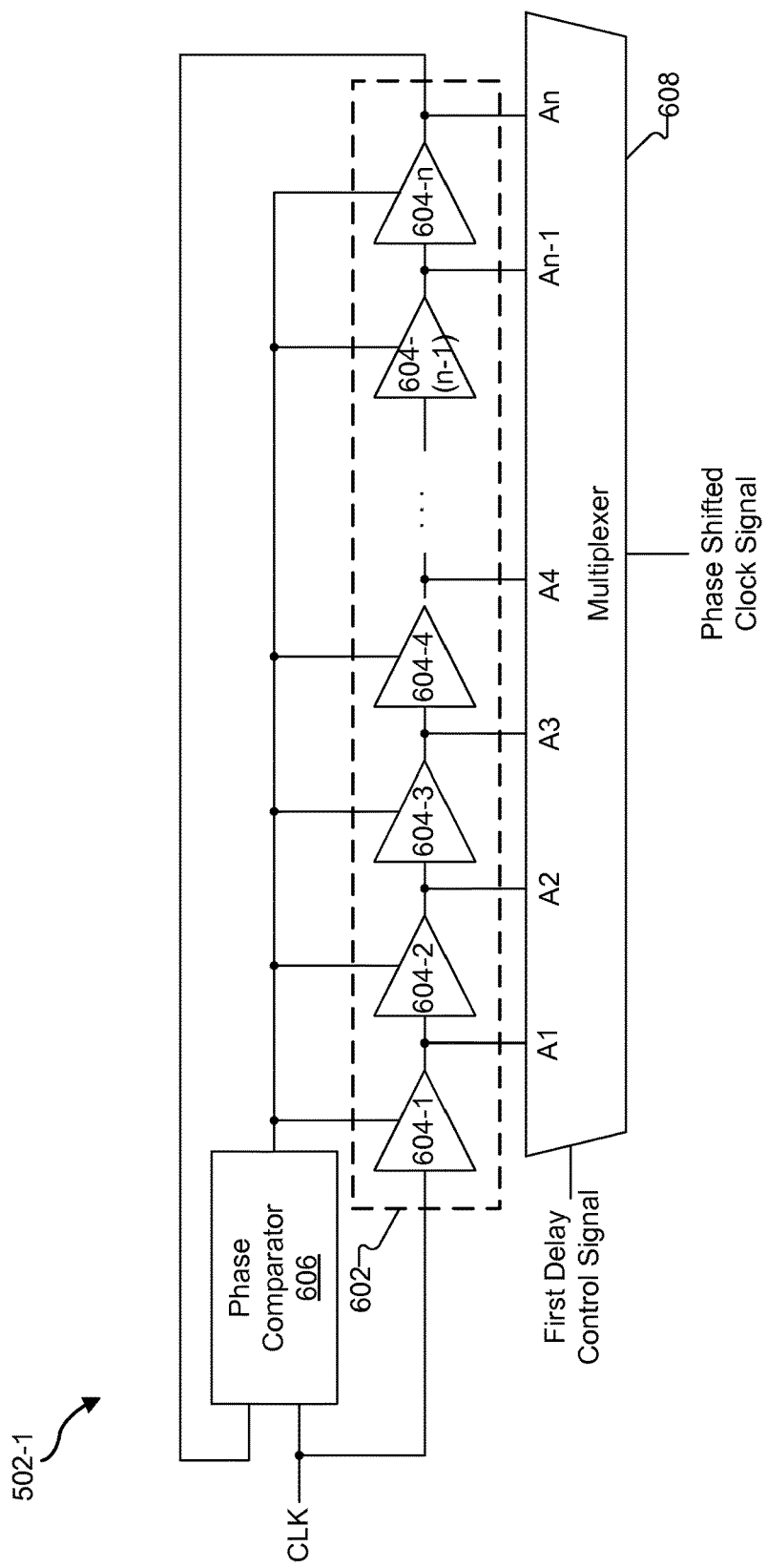
FIGS. 6-7 show enlarged views of delay-locked loop circuits according to principles described herein.
Figure 7:
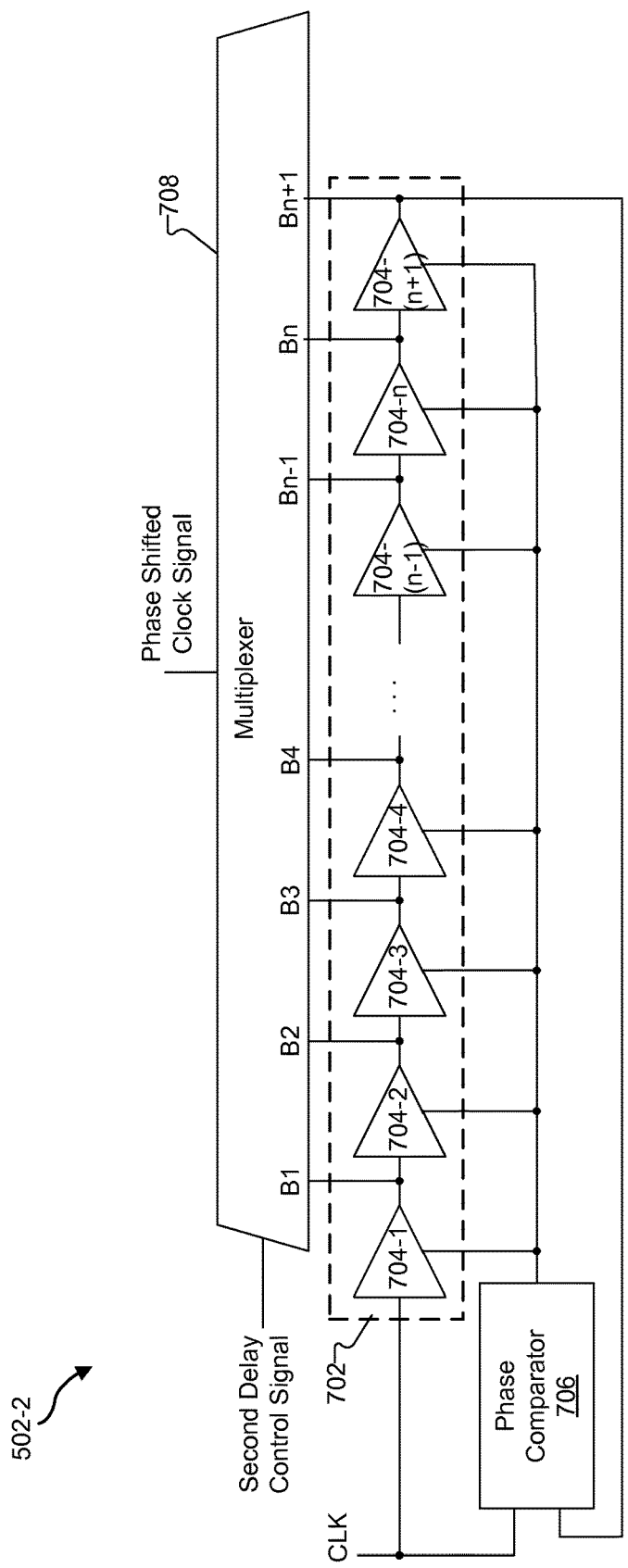

FIG. 6 shows an enlarged view of DLL circuit 502-1 and FIG. 7 shows an enlarged view of DLL circuit 502-2. DLL circuits 502 will be described with reference to FIGS. 5-7.

As shown, each DLL circuit 502 includes a delay line that includes a plurality of delay elements connected in series one with another. For example, DLL circuit 502-1 includes a delay line 602 (also referred to herein as a first delay line 602) that includes a first set of delay elements 604-1 through 604-$n$ (collectively "delay elements 604") connected in series one with another. Likewise, DLL circuit 502-2 includes a delay line 702 (also referred to herein as a second delay line 702) that includes a second set of delay elements 704-1 through 704-$(n+1)$ (collectively "delay elements 704") connected in series one with another.

As shown, the first delay element (i.e., delay element 604-1 and delay element 704-1) included in each delay line receives the clock signal as an input. As shown in FIG. 6, the clock signal is also input, together with the output of delay line 602, into a phase comparator 606. Likewise, the clock signal is input, together with the output of delay line 702, into a phase comparator 706.

Phase comparator 606 performs a phase comparison of the clock signal and the output of first delay line 602, and, based on the comparison, outputs a control voltage that adjusts a delay of each delay element 604 so that a total delay through the first delay line 602 is substantially equal to a single period of the clock signal (which is also the period of the RF signal that is ultimately output by RF transmitter circuit 304). Likewise, phase comparator 706 performs a phase comparison of the clock signal and the output of second delay line 702, and, based on the comparison, outputs a control voltage that adjusts a delay of each delay element 704 so that a total delay through the second delay line 702 is substantially equal to the single period of the clock signal.

Because the delay elements in each delay line are identically matched to each other (something that is achievable in integrated circuit manufacturing), the output of each delay element in each delay line represents an equal phase delay increment. In this manner, the transmitter phase delay can be selected through a digitally-controlled multiplexer (i.e., multiplexers 608 and 708).

To illustrate, because each delay element 604 included in delay line 602 of DLL circuit 502-1 is in series one with another, each successive delay element 604 in delay line 602 may delay the phase of the signal that is passed therethrough by an incremental amount. For example, delay element 604-1 may output a first phase shifted clock signal that is phase shifted relative to the clock signal by a baseline phase delay increment associated with delay line 602. Delay element 604-2 may receive the first phase shifted clock signal as an input and output a second phase shifted clock signal that is phase shifted relative to the clock signal by two times the baseline phase delay increment. The remaining delay elements 604 may similarly output phase shifted clock signals that are phase shifted relative to the clock signal by different integer multiples of the baseline phase delay increment. Delay elements 704 included in DLL circuit 502-2 similarly output phase shifted clock signals that are phase shifted relative to the clock signal by different integer multiples of a baseline phase delay increment associated with delay line 702.

Each delay line 602 and 702 may include any number of delay elements as may serve a particular implementation. In some examples, the number of delay elements included in a particular delay line may be determined by the period of the clock signal divided by the minimum practical delay of a single delay element. This minimum practical delay may be determined by the integrated circuit manufacturing process. To illustrate, for relatively low-cost and low-power integrated circuit manufacturing processes, such as 180 nm CMOS operating at a 1 volt power supply, the minimum achievable delay step is on the order of 500 ps. If the frequency of the clock signal is 50 MHz, then the maximum number of delay steps (i.e., the maximum number of delay elements included in the delay line) is (1/50 MHz)/(500 ps)=40.

In some examples, the number of delay elements 604 included in delay line 602 of first DLL circuit 502-1 is different than the number of delay elements 704 included in delay line 702 of second DLL circuit 502-2. For example, in FIGS. 5-7, first DLL circuit 502-1 includes n delay elements 604 and second DLL circuit 502-2 includes n+1 delay elements 704. As a specific example, first DLL circuit 502-1 may include 32 delay elements and second DLL circuit 502-2 may include 33 delay elements. It will be recognized that first DLL circuit 502-1 may alternatively include more delay elements than second DLL circuit 502-2.

Because each DLL circuit 502 includes a different number of delay elements, the baseline phase delay increment associated with each delay line 602 and 702 may differ. For example, in the particular example of FIGS. 5-7, the baseline phase delay increment associated with delay line 602 is 1/n times (i.e., multiplied by) the period of the clock signal because there are n delay elements 604. However, the baseline phase delay increment associated with delay line 702 is 1/(n+1) times the period of the clock signal because there are n+1 delay elements 704. As will be described in more detail below, having different baseline phase delay increments for each delay line 602 and 702 facilitates vernier-like adjustment (i.e., relatively fine resolution adjustment) of the power level of the RF signal output by transformer circuit 406.

As mentioned, DLL circuit 502-1 may include a multiplexer 608 and DLL circuit 502-2 may include a multiplexer 708. Multiplexer 608 receives each phase shifted clock signal output by delay elements 604 included in delay line 602 of DLL circuit 502-1. For example, multiplexer 608 receives the phase shifted clock signal output by delay element 604-1 at input port A1, the phase shifted clock signal output by delay element 604-2 at input port A2, etc. Likewise, multiplexer 708 receives each phase shifted clock signal output by delay elements 704 included in delay line 702 of DLL circuit 502-2. For example, multiplexer 708 receives the phase shifted clock signal output by delay element 704-1 at input port B1, the phase shifted clock signal output by delay element 704-2 at input port B2, etc.

Multiplexer 608 is controlled by the first delay control signal provided by control module 302 and multiplexer 708 is controlled by the second delay control signal provided by control module 302. In other words, multiplexer 608 may select and output, in accordance with the first delay control signal, a particular phase shifted clock signal included in the phase shifted clock signals output by delay elements 604. Likewise, multiplexer 708 may select and output, in accordance with the second delay control signal, a particular phase shifted clock signal included in the phase shifted clock signals output by delay elements 704.

For example, the first delay control signal may include data representative of a particular phase delay increment (e.g., a phase delay increment associated with the phase shifted clock signal output by delay element 604-2). Multiplexer 608 may accordingly select and output a phase shifted clock signal that has the particular phase delay increment (e.g., by selecting and outputting the phase shifted clock signal output by delay element 604-2).

Likewise, the second delay control signal may include data representative of a particular phase delay increment (e.g., a phase delay increment associated with the phase shifted clock signal output by delay element 704-3). Multiplexer 708 may accordingly select and output a phase shifted clock signal that has the particular phase delay increment (e.g., by selecting and outputting the phase shifted clock signal output by delay element 704-3).

As shown in FIG. 5, first switching circuit 504-1 receives the phase shifted clock signal output by multiplexer 608 and outputs a first switch signal based on the phase shifted clock signal output by multiplexer 608. The first switch signal has the same phase delay as the phase shifted clock signal output by multiplexer 608. For example, if multiplexer 608 selects and outputs the phase shifted clock signal provided by delay element 604-1, the first switch signal is phase shifted relative to the clock signal by the same phase delay increment as the phase shifted clock signal provided by delay element 604-1 (i.e., 1/n times the period of the clock signal).

Likewise, as shown in FIG. 5, second switching circuit 504-2 receives the phase shifted clock signal output by multiplexer 708 and outputs a second switch signal based on the phase shifted clock signal output by multiplexer 708. The second switch signal has the same phase delay as the phase shifted clock signal output by multiplexer 708. For example, if multiplexer 708 selects and outputs the phase shifted clock signal provided by delay element 704-1, the first switch signal is phase shifted relative to the clock signal by the same phase delay increment as the phase shifted clock signal provided by delay element 704-1 (i.e., 1/(n+1) times the period of the clock signal).

Switching circuits 504 may be implemented in any suitable manner. For example, switching circuits may be constructed to operate as an H-bridge amplifier. As such, switching circuits 504 may each include one or more bi-directional current carrying devices (e.g., a conventional CMOS digital inverter) to provide a switching operation (e.g., where switching circuits 504 can be turned ON and OFF) to control the amplitude of the RF signal. The power source, ground, switching circuits 504, and transformer circuit 406 may form a circuit loop that sets the power level of the RF signal according to the phase shifted clock signals output by multiplexers 608 and 708.

Figure 8:
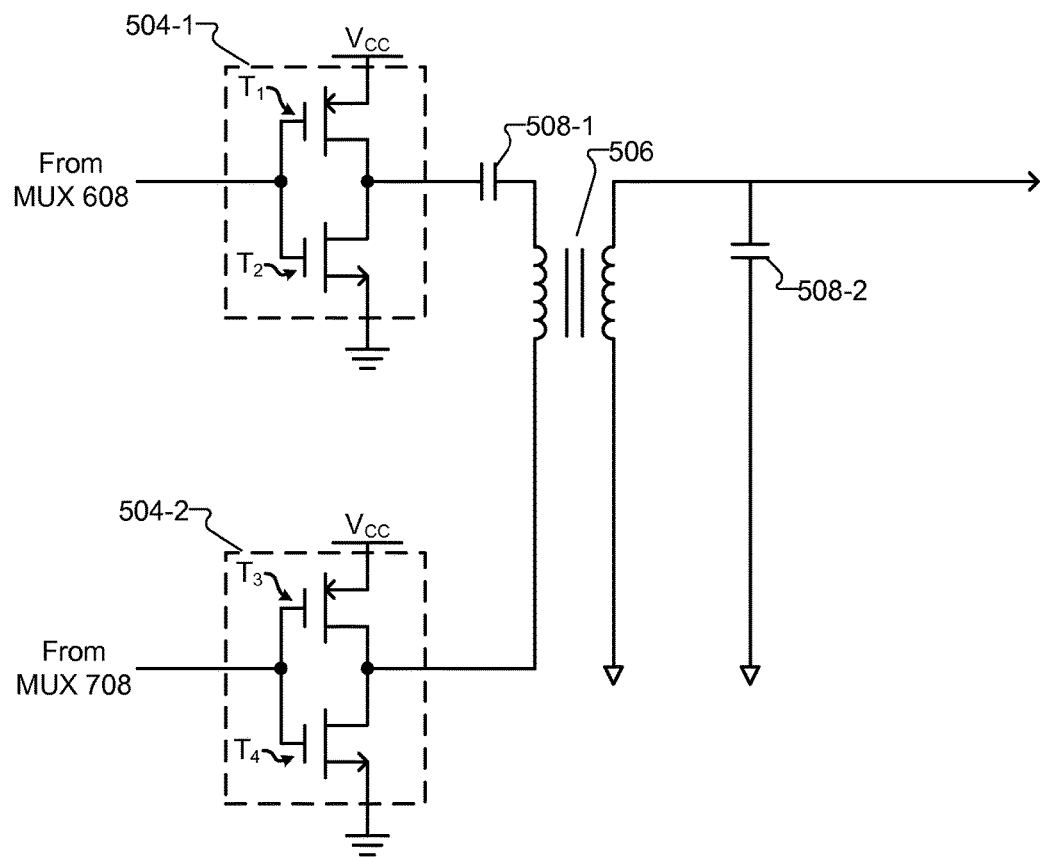
FIG. 8 shows an exemplary implementation in which switching circuits are shown as CMOS inverters according to principles described herein.

FIG. 8 shows an exemplary implementation in which switching circuits 504 are shown as CMOS inverters. Each CMOS inverter may have two transistors, with one being coupled to VCC and the other being coupled to ground. These four transistors, labeled T1, T2, T3 and T4, may form a driver configuration (e.g., an H-bridge) where transformer circuit 406, particularly the primary winding of transformer 506, is treated as a "load." Several different circuit paths exist depending on the states of the phase shifted clock signals output by multiplexers 608 and 708. For example, when the phase shifted clock signal output by multiplexer 608 is HIGH and the phase shifted clock signal output by multiplexer 708 is LOW, current from VCC of switching circuit 504-2 may be routed through transformer 506 to ground of switching circuit 504-1. When the phase shifted clock signals output by multiplexers 608 and 708 are both HIGH, the respective ends of the primary winding of transformer 506 are coupled to ground via T2 and T4. When the phase shifted clock signals output by multiplexers 608 and 708 are both LOW, the respective ends of the primary winding of transformer 506 are both coupled to VCC via T1 and T3.

Returning to FIG. 5, the first switch signal output by switching circuit 504-1 is input to a first end of transformer 506 and the second switch signal output by switching circuit 504-2 is input to a second end of transformer 506. Transformer 506 may be a loosely coupled transformer having a 1-to-N turns ratio, where N is an arbitrary value. In some examples, transformer 506 isolates switching circuits 504 from the load. Capacitors 508-1 and 508-2, which are also a part of transformer circuit 406, may be series-resonating capacitors that enable transformer 506 to operate as a double-tuned bandpass filter. Such bandpass filter advantageously eliminates the need to use additional filters downstream of transformer 506, thereby promoting energy transfer efficiency.

Transformer 506 may use the first and second switch signals to generate an RF signal for transmission to implant device 104. This may be performed in any suitable manner. For example, transformer 506 may generate the RF signal by operating in a push-pull configuration. Transformer 506 may vary the power level of the RF signal in response to a change in the first and/or second delay control signals.

Figure 9:
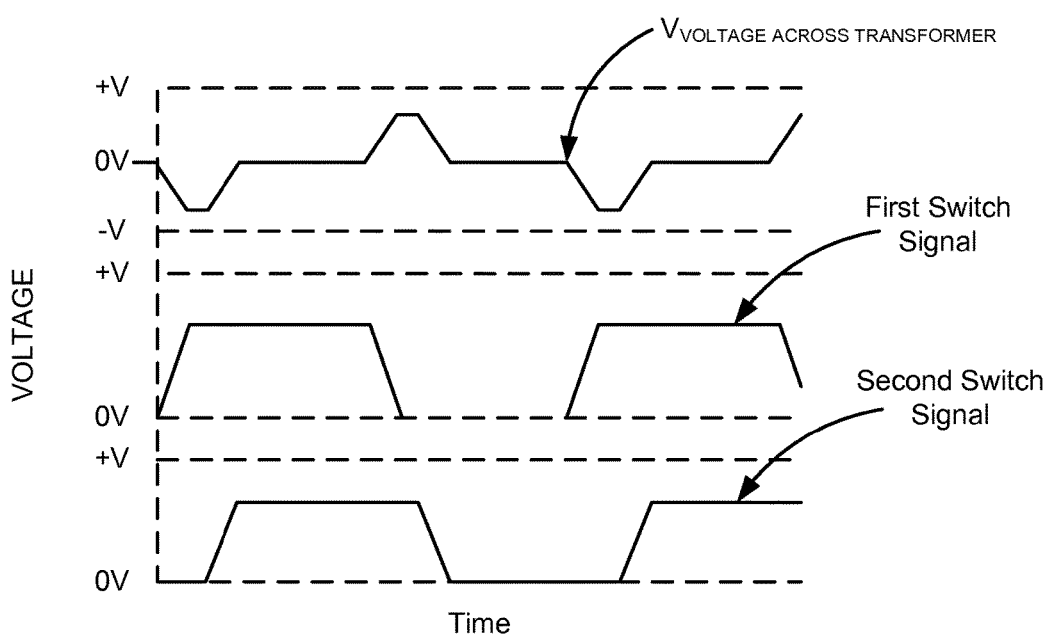
FIG. 9 illustrates an example of first and second switch signals as applied to a transformer according to principles described herein.

To illustrate, an example of the first and second switch signals as applied to transformer 506 shown in FIG. 9. The combination of the first and second switch signals may at given times within a clock cycle result in the application of a differential signal across transformer 506 of transformer circuit 406 (as shown in FIG. 9). This differential signal may be the result of a voltage difference of the first and second switch signals at transformer 506, which sets the power level of the RF signal.

In some examples, a differential voltage may exist across transformer 506 when switching circuits 504 are providing signals in opposite states; that is, one switching circuit provides a HIGH signal and the other provides a LOW signal. As shown in FIG. 9, when the first switch signal is HIGH (e.g., because switching circuit 504-1 is being driven HIGH) and the second switch signal is LOW (e.g., because switching circuit 504-2 is being drive LOW), a differential voltage (shown as the triangular portion of the waveform) may exist across transformer 506. A differential voltage may not exist across transformer 506 when switching circuits 504 output signals in the same state (e.g., both HIGH or LOW). This is shown in FIG. 9 when both the first and second switch signals are in the same state. Thus, when both the first and second switch signals are HIGH, the differential voltage is negligible, and when both the first and second switch signals are LOW, the differential voltage is also negligible. Moreover, RF signal power level is a function of the relative phases of the two switch signals. In other words, if the two signals are at opposite levels for a large fraction of the clock (carrier) cycle, transformer 506 will be conducting for most of the cycle and a relatively large power output will result. On the other hand, if the switch signals are at the same level for a large portion of the carrier cycle, the transformer 506 will be in a conducting state for a small fraction of the cycle and a relatively smaller power output will result. Thus by adjusting the relative phases of the two switch signals, adjustment of RF power is achieved.

The differential signal may contain frequency components at the fundamental frequency of the carrier, and all odd harmonics. Even harmonics may not be present in the differential signal because of a balanced operation of switching circuits 504. That is, switching circuits 504 are balanced because they are substantially identical and symmetrically driven. Moreover, such balance or symmetric driving of the switching circuits may enable addition/subtraction of the first and second switch signals to occur in transformer circuit 406.

As mentioned, control module 302 may provide the first and second delay control signals that direct DLL circuits 502 to select and output the phase shifted clock signals used by switching circuits 504 to generate the first and second switch signals. Hence, control module 302 may dynamically adjust the power level of the RF signal output by RF transmitter circuit 304 by dynamically adjusting at least one of the first and second delay control signals.

For example, control module 302 may detect a condition (e.g., a change in stimulation needs) associated with implant device 104 that results in a change in an amount of power needed by implant device 104. In response, control module 302 may adjust at least one of the first and second delay control signals in order to dynamically adjust the power level of the RF signal. This may be performed in any suitable manner. For example, control module 302 may adjust a delay control signal by providing one or more different data words in the delay control signal.

To illustrate, the first delay control signal may initially include data representative of a first phase delay increment (e.g., a phase delay increment associated with the phase shifted clock signal output by delay element 604-2). Multiplexer 608 may accordingly select and output a phase shifted clock signal that has the first phase delay increment (e.g., by selecting and outputting the phase shifted clock signal output by delay element 604-2).

Control module 302 may subsequently adjust the first delay control signal may by replacing the data representative of a first phase delay increment with data representative of a second phase delay increment (e.g., a phase delay increment associated with the phase shifted clock signal output by delay element 604-1). Multiplexer 608 may detect this change in the first delay control signal, and, in response, adjust the phase shifted clock signal that it outputs by selecting and outputting a phase shifted clock signal that has the second phase delay increment (e.g., by selecting and outputting the phase shifted clock signal output by delay element 604-1). By so doing, control module 302 may adjust the power level of the RF signal.

As mentioned, the systems and methods described herein may facilitate vernier-like adjustment (i.e., relatively fine resolution adjustment) of the power level of the RF signal output by transformer circuit 406. For example, in the examples provided herein wherein the baseline phase delay increment associated with delay line 602 is $1/n$ times the period of the clock signal and the baseline phase delay increment associated with delay line 702 is $1/(n+1)$ times the period of the clock signal, multiplexer 608 may select and output the phase shifted clock signal provided by delay element 604-1 and multiplexer 708 may select and output the phase shifted clock signal provided by delay element 704-1. In this example, the difference in delay between the two phase shifted clock signals would be $1/n - 1/(n+1)$ or $1/(n^2+n)$. This represents the minimum delay step, so the total number of delay steps would be 1 over that, or $n^2+n$. In the case example where the number of delay elements in delay line 602 is 32 and the number of delay elements in delay line 702 is 33, this equals 1056 possible delay increments that may be selected by control module 302 in order to adjust the power level of the RF signal output by transformer circuit 406.

While two DLL circuits 502 have been described herein, it will be recognized that a single DLL circuit 502 (e.g., DLL circuit 502-2) may alternatively be used. In this scenario, the first switch signal output by switching circuit 504-1 has the same phase as the clock signal, and the second switch signal output by switching circuit 504-2 is phase shifted with respect to the clock signal in order to adjust the power level of the RF signal output by transformer circuit 406.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:
1. An apparatus located external to a patient and that comprises:
a first delay-locked loop circuit that
receives a clock signal,
generates a first set of phase shifted clock signals each phase shifted relative to the clock signal by a different phase delay increment included in a first set of phase delay increments, and outputs, in accordance with a first delay control signal,
a first phase shifted clock signal included in the first
set of phase shifted clock signals and that is phase
shifted relative to the clock signal by a first phase
delay increment included in the first set of phase
delay increments;
a second delay-locked loop circuit that
receives the clock signal,
generates a second set of phase shifted clock signals
each phase shifted relative to the clock signal by a
different phase delay increment included in a second
set of phase delay increments, and
outputs, in accordance with a second delay control
signal, a second phase shifted clock signal included
in the second set of phase shifted clock signals and
that is phase shifted relative to the clock signal by a
second phase delay increment included in the second
set of phase delay increments;
a first switching circuit that receives the first phase shifted
clock signal from the first delay-locked loop circuit and
outputs a first switch signal based on the first phase
shifted clock signal, the first switch signal being phase
shifted relative to the clock signal by the first phase
delay increment;
a second switching circuit that receives the second phase
shifted clock signal from the second delay-locked loop
circuit and outputs a second switch signal based on the
second phase shifted clock signal, the second switch
signal being phase shifted relative to the clock signal by
the second phase delay increment; and
a transformer circuit connected to the first and second
switching circuits and that uses the first and second
switch signals to generate an RF signal for transmission
to an implant device implanted in the patient, the RF
signal having a power level that is set based on the first
and second phase delay increments.

2. The apparatus of claim 1, further comprising a control module that:
provides the first and second delay control signals; and
dynamically adjusts the power level of the RF signal by
dynamically adjusting at least one of the first and
second delay control signals.

3. The apparatus of claim 2, wherein the control module:
detects a condition associated with the implant device that
results in a change in an amount of power needed by the
implant device; and
adjusts, in response to the detection of the condition, at
least one of the first and second delay control signals in
order to dynamically adjust the power level of the RF
signal.

4. The apparatus of claim 1, wherein:
the first delay-locked loop circuit:
detects a change in the first delay control signal, and
adjusts, in response to the change in the first delay
control signal, the first phase shifted clock signal to
be phase shifted relative to the clock signal by a third
phase delay increment included in the first set of
phase delay increments;
the first switching circuit adjusts, in response to the
adjustment of the first phase shifted clock signal, the
first switch signal to be phase shifted relative to the
clock signal by the third phase delay increment; and
wherein the adjustment of the first and second switch
signals by the second and third phase delay increments
adjusts the power level of the RF signal generated by
the transformer circuit.

5. The apparatus of claim 4, wherein:
the second delay-locked loop circuit:
detects a change in the second delay control signal, and
adjusts, in response to the change in the second delay
control signal, the second phase shifted clock signal
to be phase shifted relative to the clock signal by a
fourth phase delay increment included in the second
set of phase delay increments;
the second switching circuit adjusts, in response to the
adjustment of the second phase shifted clock signal, the
second switch signal to be phase shifted relative to the
clock signal by the fourth phase delay increment; and
wherein the adjustment of the second switch signal by the
fourth phase delay increment adjusts the power level of
the RF signal generated by the transformer circuit.

6. The apparatus of claim 1, wherein:
the first delay-locked loop circuit comprises a first delay
line that includes a first set of delay elements connected
in series one with another, wherein each delay element
included in the first set of delay elements outputs a
different phase shifted clock signal included in the first
set of phase shifted clock signals; and
the second delay-locked loop circuit comprises a second
delay line that includes a second set of delay elements
connected in series one with another, wherein each
delay element included in the second set of delay
elements outputs a different phase shifted clock signal
included in the second set of phase shifted clock
signals.

7. The apparatus of claim 6, wherein:
the first delay-locked loop circuit further comprises a first
multiplexer that receives the first delay control signal
and each phase shifted clock signal included in the first
set of phase shifted clock signals and performs the
outputting of the first phase shifted clock signal in
accordance with the first delay control signal; and
the second delay-locked loop circuit further comprises a
second multiplexer that receives the second delay control signal and each phase shifted clock signal included
in the second set of phase shifted clock signals and
performs the outputting of the second phase shifted
clock signal in accordance with the second delay control signal.

8. The apparatus of claim 6, wherein the second set of
delay elements includes a different number of delay elements than the first set of delay elements.

9. The apparatus of claim 6, wherein:
the first delay-locked loop circuit further comprises a first
phase comparator that
receives, as inputs, the clock signal and an output of the
first delay line, and
outputs, based on a phase comparison of the clock
signal and the output of the first delay line, a first
control voltage that adjusts a delay of each delay
element included in the first set of delay elements so
that a total delay through the first delay line is
substantially equal to a single period of the clock
signal; and
the second delay-locked loop circuit further comprises a
second phase comparator that
receives, as inputs, the clock signal and an output of the
second delay line, and
outputs, based on a phase comparison of the clock
signal and the output of the second delay line, a
second control voltage that adjusts a delay of each
delay element included in the second set of delay elements so that a total delay through the second delay line is substantially equal to the single period of the clock signal.

10. The apparatus of claim 6, wherein:
the first set of delay elements are matched one with another such that each phase shifted clock signal included in the first set of phase shifted clock signals is phase shifted by a different integer multiple of a baseline phase delay increment associated with the first set of delay elements; and
the second set of delay elements are matched one with another such that each phase shifted clock signal included in the second set of phase shifted clock signals is phase shifted by a different integer multiple of a baseline phase delay increment associated with the second set of delay elements.

11. The apparatus of claim 1, further comprising a clock source that provides the clock signal.

12. The apparatus of claim 1, wherein the RF signal provides power to the implant device.

13. The apparatus of claim 1, wherein the transformer circuit provides the RF signal to a coil for transmission to the implant device.

14. The apparatus of claim 1, wherein control data for the implant device is modulated onto the RF signal.

15. The apparatus of claim 1, wherein the implant device is a cochlear implant.

16. An apparatus located external to a patient and that comprises:
a radio frequency ("RF") transmitter circuit that generates an RF signal for transmission to an implant device implanted within the patient by
generating a first switch signal that is phase shifted relative to a clock signal by a first phase delay increment,
generating a second switch signal that is phase shifted relative to the clock signal by a second phase delay increment that is different than the first phase delay increment, and
applying the first and second switch signals to a transformer operating in a push-pull configuration; and
a control module communicatively coupled to the RF transmitter circuit and that directs the RF transmitter circuit to dynamically adjust a power level of the RF signal by directing the RF transmitter circuit to adjust the first phase delay increment to be a first interval multiple of a first baseline delay increment and the second phase delay increment to be a second interval multiple of a second baseline delay increment that is different than the first baseline delay increment.

17. The apparatus of claim 16, wherein the implant device is a cochlear implant.

18. The apparatus of claim 16, wherein the RF signal provides power to the implant device.

19. A method comprising:
generating, by a radio frequency ("RF") transmitter circuit included in an apparatus located external to a patient, an RF signal for transmission to an implant device implanted within the patient by
generating a first switch signal that is phase shifted relative to a clock signal by a first phase delay increment,
generating a second switch signal that is phase shifted relative to the clock signal by a second phase delay increment that is different than the first phase delay increment, and
applying the first and second switch signals to a transformer operating in a push-pull configuration; and
directing, by a control module included in the apparatus, the transmitter circuit to dynamically adjust a power level of the RF signal by directing the transmitter circuit to adjust the first phase delay increment to be a first interval multiple of a first baseline delay increment and the second phase delay increment to be a second interval multiple of a second baseline delay increment that is different than the first baseline delay increment.

20. The method of claim 19, wherein the implant device is a cochlear implant.

* * * * *